United States Patent [19]

Flemer, III

[11] Plant 4,458

[45] Sep. 4, 1979

[54] *HYDRANGEA QUERCIFOLIA*

[75] Inventor: William Flemer, III, Princeton, N.J.

[73] Assignee: Treesearch, Kingston, N.J.

[21] Appl. No.: 952,561

[22] Filed: Oct. 18, 1978

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Frank B. Robb

[57] ABSTRACT

There is disclosed an *Hydrangea quercifolia* plant, having pure white color blooms with perfect and abundant sterile florets on the same panicle, the habit being low and compact, up to one and one-half meters in height with spreading compact almost hemispherical outline, the non-pendant blooms being borne on strong erect stems.

1 Drawing Figure

DESCRIPTION OF THE DISCLOSURE

In my nursery greenhouses in South Brunswick, N.J., seed of Hydrangea are planted each year and in this particular instance, the variety hereof was found in a cultivated block of Oakleaf hydrangea. It was open pollinated and especially noticeable because of its distinctive white color and larger than normal number of sterile florets presenting a showy appearance.

After selection of this hydrangea plant for that reason and because of its low compact habit, nearly hemispherical general plant appearance, blooms appearing on tall, erect, strong, stems, I have caused the same to be asexually reproduced and found that it comes true in successive propagation.

After selecting the instant plant, which because of its strong white color and abundant sterile florets, I have designated "Snow Queen", I have caused the same to be asexually reproduced, at my nursery at Princeton, N.J., where the plants of this variety have withstood temperatures of 10 degress F., below zero, attesting to the hardiness thereof.

The plants have been asexually reproduced to sufficient extent as to establish that the principal characteristics hereinafter set forth in detail come true and consistently in succeeding propagations, to satisfy my critical criteria.

While the drawing appended hereto and forming a part hereof, accurately discloses the plant as to its shape, habit, leaf form, flower color and form, the leaf color cannot be reproduced exactly as it is in nature, if the white color of the bloom is to be shown in its true relationship. If the reproduction was made to depict leaf color as it is in its natural state, then the white color of the bloom would not be accurately disclosed. Therefore I have chosen to show the bloom as it actually appears, sacrificing some accuracy in color of the foliage.

The leaves are not distinct from the usual *quercifolia*, which are more yellow green than the disclosure hereof, the instant variety likewise having the more yellow green leaves or foliage, which appear as a strong to moderate green 7.5 G 5/8 to 7.5 G 4/7 in the reproduction which forms the drawing, the leaf of the actual plant being more nearly described as for new foliage, on the upper side 5 GY 5/6 with the under side 2.5 GY 6/8, the older foliage thereafter being somewhat darker, the upper side described as 7.5 GY 4/4 with the under side 2.5 GY 5/5.

It is noted that the applicant does not claim any distinct differences in the foliage color but on the other hand states that the blooms are more showy than the parent from which the plant was open pollinated and that there are more sterile florets, usually 50 to 60 in each bloom panicle, yet retaining erect flower clusters.

The color reproduction forming the drawing hereof is as nearly accurate as possible to make the same with available color photography techniques, and clearly showing the blooms as they actually appear, color designations where used in reference to a known scale being those determined by comparison with the Nickerson Color Fan, which was published by Munsell Color Co. of Baltimore, Md.

There follows a detailed description of my new variety of *Hydrangea quercifolia,* specific color terms set forth being those of the reference color fan, other common descriptive terms being used were applicable, these usually being of ordinary dictionary significance.

Breeding — seedling:

*Seed parent.*—*Hydrangea quercifolia* (Oakleaf Hydrangea).

*Pollen parent.*—Open pollinated.

Classification: Bush; little branched; compact.

Propagation: Holds its distinguishing characteristics through succeeding propagations by cuttings.

Locality where grown and observed: South Brunswick Township, N.J.

Temperature tolerance: Has withstood 10 degrees F. below zero during growing at Princeton, N.J. in South Brunswick Township.

Flower:

*Blooms.*—Sterile and perfect florets in the same panicle.

*Size.*—Length of panicle — 20 to 25 cm. Width of panicle 10 to 12 cm.

*Form.*—Paniculate, 50 to 60 sterile florets per panicle.

*Color.*—Pure white turning pinkish as it becomes older.

*Blooming period.*—June 15 to July 30, but lasting longer, however increasing discoloration taking place thereafter.

Growth habit: Vigorous — compact.

Rooting: Coordinate; dense.

Blooming habit: Abundant flowers.

Blooming season: As before stated June 15 to July 30 lasting longer but not suitable for forcing.

Foliage:

*Quantity.*—Abundant.

*Color.*—New foliage — upper side (as shown in drawing 7.5 G 5/8 to 7.5 G 4/7) on the plant 5 GY 5/6. Under side — 2.5 GY 6/8. Old foliage — (not shown in photograph). Upper side — moderate olive green 7.5 GY 4/4. Under side — strong yellow green 2.5 GY 5/5.

*Shape.*—Oak leaf shaped with 5 major lobes, each pointed at the top.

*Texture.*—Upper side — leathery; moderately corrugated. Under side — velvety.

*Edge of margin.*—Shape — irregularly serrate; serrations terminating in minute glands.

I claim:

1. A new and distinct variety of *Hydrangea quercifolia* plant substantially as herein shown and described, characterized particularly as to novelty by the unique combination of very showy, white blooms, having abundant sterile florets usually about fifty to sixty in number, the blooms borne on strong, erect stems in upright nonpendant position, to a height of about one and one half meters, the low compact bush being generally hemispherical in overall appearance.

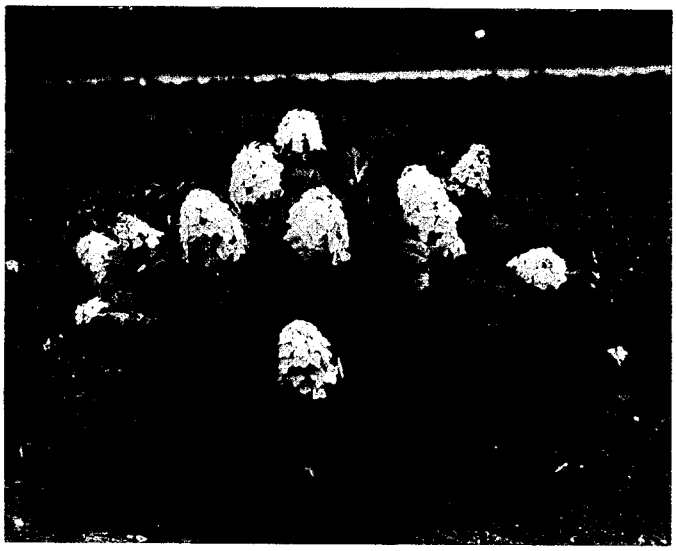

* * * * *